United States Patent
Suzuki

(10) Patent No.: US 7,767,878 B2
(45) Date of Patent: Aug. 3, 2010

(54) DISPOSABLE ABSORBENT ARTICLE

(75) Inventor: Taichiro Suzuki, Tsurugi-cho (JP)

(73) Assignee: Livedo Corporation, Ehime (JP)

( * ) Notice: Subject to any disclaimer, the term of this patent is extended or adjusted under 35 U.S.C. 154(b) by 0 days.

(21) Appl. No.: 10/548,863

(22) PCT Filed: Mar. 12, 2004

(86) PCT No.: PCT/JP2004/003349

§ 371 (c)(1),
(2), (4) Date: Sep. 8, 2005

(87) PCT Pub. No.: WO2004/080361

PCT Pub. Date: Sep. 23, 2004

(65) Prior Publication Data

US 2006/0184146 A1 Aug. 17, 2006

(30) Foreign Application Priority Data

Mar. 12, 2003 (JP) ............................ 2003-067287
Jun. 19, 2003 (JP) ............................ 2003-175148

(51) Int. Cl.
*A61F 13/15* (2006.01)

(52) U.S. Cl. ...................... 604/372; 604/374; 604/375; 604/378; 604/379; 604/380; 604/368; 604/365; 604/385.101

(58) Field of Classification Search ................. 604/372, 604/374, 375, 378, 379, 380, 385.101, 368, 604/365

See application file for complete search history.

(56) References Cited

U.S. PATENT DOCUMENTS

| | | | |
|---|---|---|---|
| 4,055,180 A | | 10/1977 | Karami |
| 4,988,345 A | * | 1/1991 | Reising ...................... 604/368 |
| 5,562,645 A | | 10/1996 | Tanzer et al. |
| 5,601,542 A | | 2/1997 | Melius et al. |
| 5,855,572 A | | 1/1999 | Schmidt |
| 5,938,650 A | | 8/1999 | Baer et al. |
| 6,080,909 A | | 6/2000 | Oesterdahl et al. |
| 6,432,094 B1 | | 8/2002 | Fujioka et al. |
| 6,646,179 B1 | * | 11/2003 | Melius et al. ................ 604/368 |
| 2001/0023339 A1 | | 9/2001 | Onishi |
| 2002/0165509 A1 | * | 11/2002 | Baer et al. ................... 604/368 |

FOREIGN PATENT DOCUMENTS

| | | |
|---|---|---|
| EP | 0 615 736 | 9/1994 |
| EP | 0 958 802 | 11/1999 |
| JP | 2-26555 | 1/1990 |
| JP | 7-231911 | 9/1995 |

(Continued)

*Primary Examiner*—Jacqueline F. Stephens
(74) *Attorney, Agent, or Firm*—Jordan and Hamburg LLP

(57) ABSTRACT

A disposable absorbent article includes an absorbent mat between a liquid-permeable top sheet and a liquid-impermeable back sheet. The absorbent mat includes a sheet-shaped water-absorbent layer that contains a water-absorbent resin powder but that does not contain pulp fibers; and a fiber assembly layer that contains a water-absorbent resin powder and pulp fibers in this order from a top sheet side. The sheet-shaped water-absorbent layer includes a plurality of water-absorbent resin presence regions in each of which the water-absorbent resin powder is wrapped; and a plurality of water-absorbent resin powder absence regions each being formed between the two adjacent water-absorbent resin powder presence regions.

16 Claims, 12 Drawing Sheets

FOREIGN PATENT DOCUMENTS

| | | |
|---|---|---|
| JP | 9-504210 | 4/1997 |
| JP | 2001-46435 | 2/2001 |
| JP | 2001-245926 | 9/2001 |
| JP | 2002-224161 | 8/2002 |
| JP | 2003-070842 | 3/2003 |
| WO | WO-95/22952 | 8/1995 |
| WO | WO-97/34558 | 9/1997 |
| WO | WO-98/36720 | 8/1998 |
| WO | WO-00/71790 | 11/2000 |
| WO | WO 01/89439 | 11/2001 |

\* cited by examiner

Fig. 9
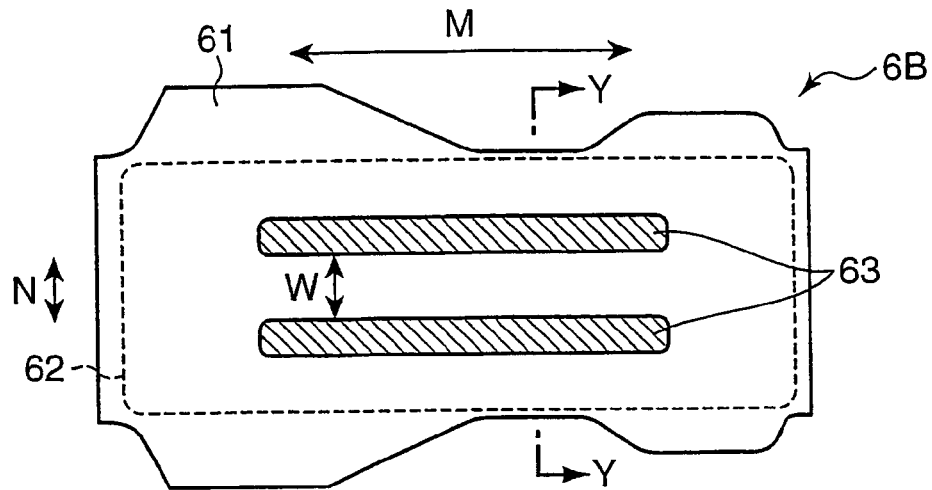
(a)
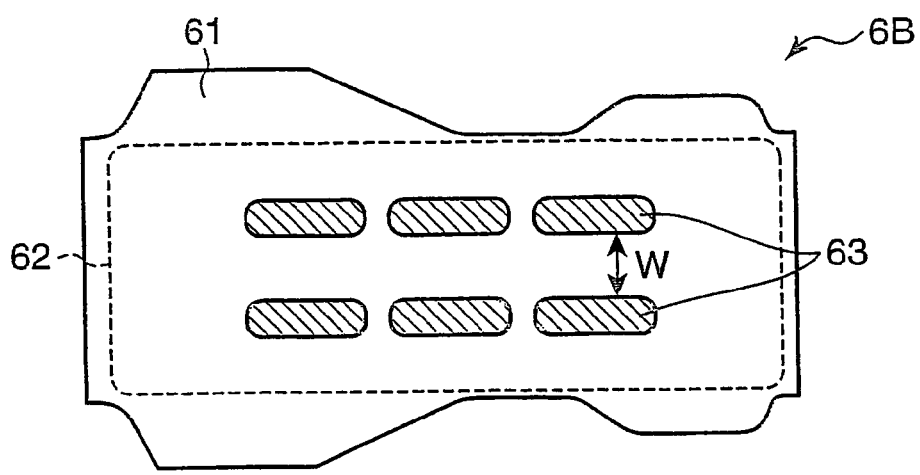
(b)
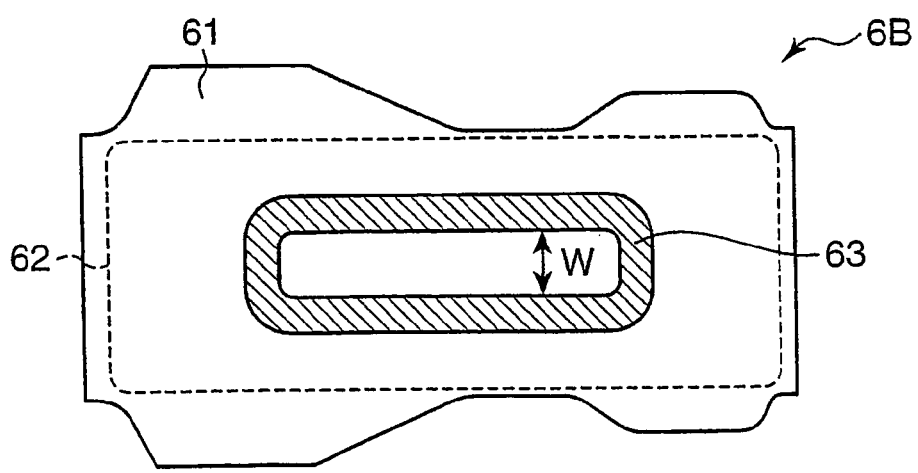
(c)

DISPOSABLE ABSORBENT ARTICLE

TECHNICAL FIELD

The present invention relates to disposable absorbent articles such as disposable diapers and disposable pants.

BACKGROUND ART

In recent years, among fields of sanitary materials using disposable absorbent articles such as disposable diapers, disposable pants, and sanitary napkins, particularly in the field of adult disposable diapers necessary for nursing care for elderly people in relation to excretion, an absorbent article having a high absorbing capacity to ensure long-time use and having a shape stability to ensure shape retainability during use is desired so as to prevent a user who wears a diaper from being awaken for changing diapers a number of times and so as to reduce the work burden on caregivers.

A conventionally available absorbent article includes an absorbent between a liquid-permeable top sheet and a liquid-impermeable back sheet. As this absorbent, there has been used an absorbent mat obtained by forming fibrillated pulp fibers, absorbent resin powder, thermoplastic fibers, or the like into a mat, and fixedly wrapping up the mat in thin paper or the like.

In order to improve the absorbing performance of such an absorbent article, there has been proposed a method for increasing the amount of the absorbent resin powder contained in the absorbent mat. However, the swelling absorbent resin powder often causes the absorbent mat to get out of shape.

Further, by increasing the amount of the fibrillated pulp fibers that form the absorbent mat, the absorbing performance of the mat can be improved. However, if the amount of the fibrillated pulp fibers in the absorbent mat is increased, the mat is thicker. As a result, the user disadvantageously feels stiff in the hip joint and feels quite uncomfortable after long-time use. In addition, if the amount of the pulp fibers is increased, a phenomenon tends to occur that a body fluid such as urine once absorbed by the mat flows back from within the mat toward the top sheet. The body fluid thus flowing back adversely influences the skin of the user. The influence is particularly serious when the user uses the absorbent article for a long time.

As an absorbent article that prevents the backflow of the body fluid, there has been proposed so far an absorbent article that includes an absorbent material having a water-absorbent layer that contains water-absorbent resin between a liquid-permeable top sheet and a liquid-impermeable leak-proof sheet (JP-A 2002-224161). According to this technique, a material composed of a water-absorbent resin and a fibrous base material is used as the absorbent material, and another water-absorbent resin layer is provided between the liquid-permeable top sheet and the surface of the absorbent material.

The water-absorbent resin layer according to the above technique is formed so that the water-absorbent resin is independently dispersed or so that the water-absorbent resin is held between the water-absorbent sheets of cellulose fibers or the like. Thus, even if the layer contributes to backflow prevention, the shape stability is not at all considered. If the water-absorbent resin powder absorbs the body fluid and swells, the high water-absorbent resin layer may possibly get out of shape.

Further, as a very thin absorbent material that does not get out of shape after absorbing water, a very thin absorbent sheet body that does not contain pulp fiber other than nonwoven fabrics and is formed so that a water-absorbent resin powder is held between two nonwoven fabrics by a web-shaped hot melt adhesive has been proposed by the applicant of the present application (WO 01/89439).

In this technique, since the water-absorbent resin powder is fixedly retained by the web-shaped hot melt adhesive, the sheet body does not get out of shape. In addition, since the sheet body is very thin, a user who wears an absorbent article using this absorbent mat as an absorbent feels quite comfortable. However, taking into consideration the long-time use of the absorbent article that employs this absorbent mat as an absorbent, it is necessary to ensure a higher absorbing capacity. In order to ensure the higher absorbing capacity, a method for providing multilayer absorbent sheet bodies to be used as the absorbent mat or for increasing an area per absorbent sheet body or an amount of the water-absorbent resin powder per absorbent sheet may be considered. However, if a number of absorbent sheet bodies are used or the amount of the water-absorbent resin powder per absorbent sheet body is increased, a ratio of the water-absorbent resin powder contained in the entire absorbent mat becomes increased. As a result, the mat disadvantageously becomes a stiff absorbent mat, which makes the user feel stiff. In addition, to increase the area per absorbent sheet body, it is required to increase an area of the disposable absorbent article itself accordingly. This is disadvantageous not only in its production but also in usability.

Moreover, the main component of the absorbent sheet body that exhibits the absorbing performance is the water-absorbent resin powder. Therefore, the absorbent sheet body is inferior in water absorption speed to a conventional absorbent mat that is composed mainly of pulp fiber.

The present invention has been completed in view of these circumstances. It is an object of the present invention to provide a disposable absorbent article including an absorbent mat that can promptly absorb a body fluid such as urine, that has a high absorbing performance enabling long-time use, that hardly gets out of shape even if absorbing a body fluid, that hardly causes backflow of the body fluid, and that can make a user who wears the article feel comfortable.

DISCLOSURE OF THE INVENTION

A disposable absorbent article of the present invention comprises an absorbent mat between a liquid-permeable top sheet and a liquid-impermeable back sheet, wherein:

the absorbent mat includes a sheet-shaped water-absorbent layer that contains a water-absorbent resin powder but that does not contain pulp fibers; and a fiber assembly layer that contains a water-absorbent resin powder and pulp fibers in this order from a top sheet side; and the sheet-shaped water-absorbent layer includes a plurality of water-absorbent resin presence regions in each of which the water-absorbent resin powder is wrapped; and a plurality of water-absorbent resin powder absence regions each being formed between the two adjacent water-absorbent resin powder presence regions.

By employing such a formation, the absorbing performance can be improved. Therefore, even if the article is used for a long time, the article can sufficiently exhibit the high absorbing performance and suppress the backflow of the body fluid.

BRIEF DESCRIPTION OF THE DRAWINGS

FIGS. 9(a) to 9(c) are plan views of the fiber assembly having openings.

BEST MODE FOR CARRYING OUT THE INVENTION

Figure 1:
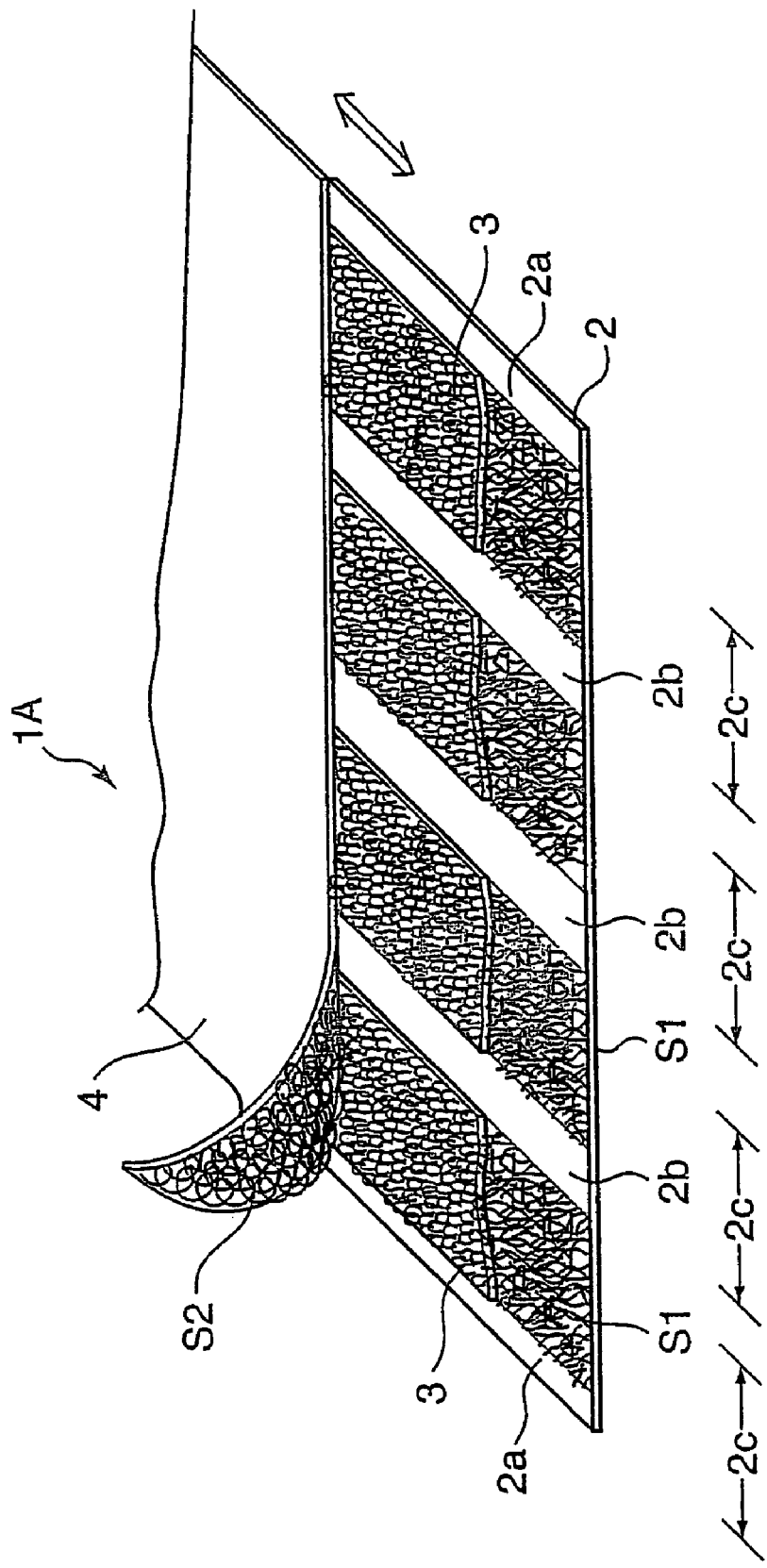
FIG. 1 is a partially cut-out perspective view of a sheet-shaped water-absorbent layer according to the present invention.

A disposable absorbent article according to the present invention comprises an absorbent mat between a liquid-permeable top sheet and a liquid-impermeable back sheet. The present invention has the greatest features in that the absorbent mat includes a sheet-shaped water-absorbent layer that contains a water-absorbent resin powder but does not contain pulp fibers; and a fiber assembly layer that contains a water-absorbent resin powder and pulp fibers in this order from a top sheet side; and the sheet-shaped water-absorbent layer includes a plurality of water-absorbent resin powder presence regions in each of which the water-absorbent resin powder is wrapped; and a plurality of water-absorbent resin absence regions each being formed between the two adjacent water-absorbent resin powder presence regions.

By employing the absorbent mat thus formed, it is possible to secure the amount of water absorption which enables long-time use and to prevent the deterioration of user's comfortableness due to the backflow of a body fluid or the like.

First, the fiber assembly layer, as one constituent element of the absorbent mat, will be described. This fiber assembly layer is provided below the sheet-shaped water-absorbent layer in the absorbent mat according to the present invention, and is essential to secure the amount of water absorption that enables long-time use.

The fiber assembly layer is composed of split pulp fibers, thermofusible fibers, and a water-absorbent resin powder dispersed in these fibers. The fiber assembly layer is formed by wrapping up the integrally formed one of these materials in thin paper (e.g., tissue paper).

As the water-absorbent resin powder dispersed in the fiber assembly layer, the same powder as that contained in the sheet-shaped water-absorbent layer, to be described later, can be used. The amount of the water-absorbent resin used therein may preferably be in the range of 15 mass % or greater to 90 mass % or smaller, relative to the amount of the split pulp fibers used in the fiber assembly layer. If the amount of the water-absorbent resin is greater than 90 mass %, the resin content is excessively high, which gives a wearer stiff impression. In addition, the swelling water-absorbent resin often unfavorably causes the layer to get out of shape. If the amount of the water-absorbent resin is smaller than 15 mass %, the resin content is excessively low, so that the resin cannot effectively contribute to increasing the amount of water absorption.

As the split pulp fibers that are fibers forming the fiber assembly layer, well-known pulp fibers can be used. As the thermofusible fibers used to improve shape retainability, polyolefin fibers formed of polyethylene, polypropylene, or the like; polyester fibers; composite fibers, or the like can be used.

The fibers and the water-absorbent resin powder are mixed up, thereby integrally forming the fiber assembly layer. Alternatively, after the fibers are formed, the water-absorbent resin powder is dispersed into the formed fibers to give the fiber assembly layer. It is preferable to stabilize the shape of the fiber assembly layer thus integrated by applying a mechanical pressure thereto while applying a heat thereto. Thereafter, the fiber assembly layer is wrapped up in thin paper. The thin paper may be tissue paper or the like. However, the thin paper is not particularly limited to the tissue paper, so long as the thin paper can permeate a body fluid. An entire plane shape of the fiber assembly layer may appropriately be determined according to the applications, and may be, for example, gourd-shaped, rectangular, or hourglass-shaped.

Figure 2:
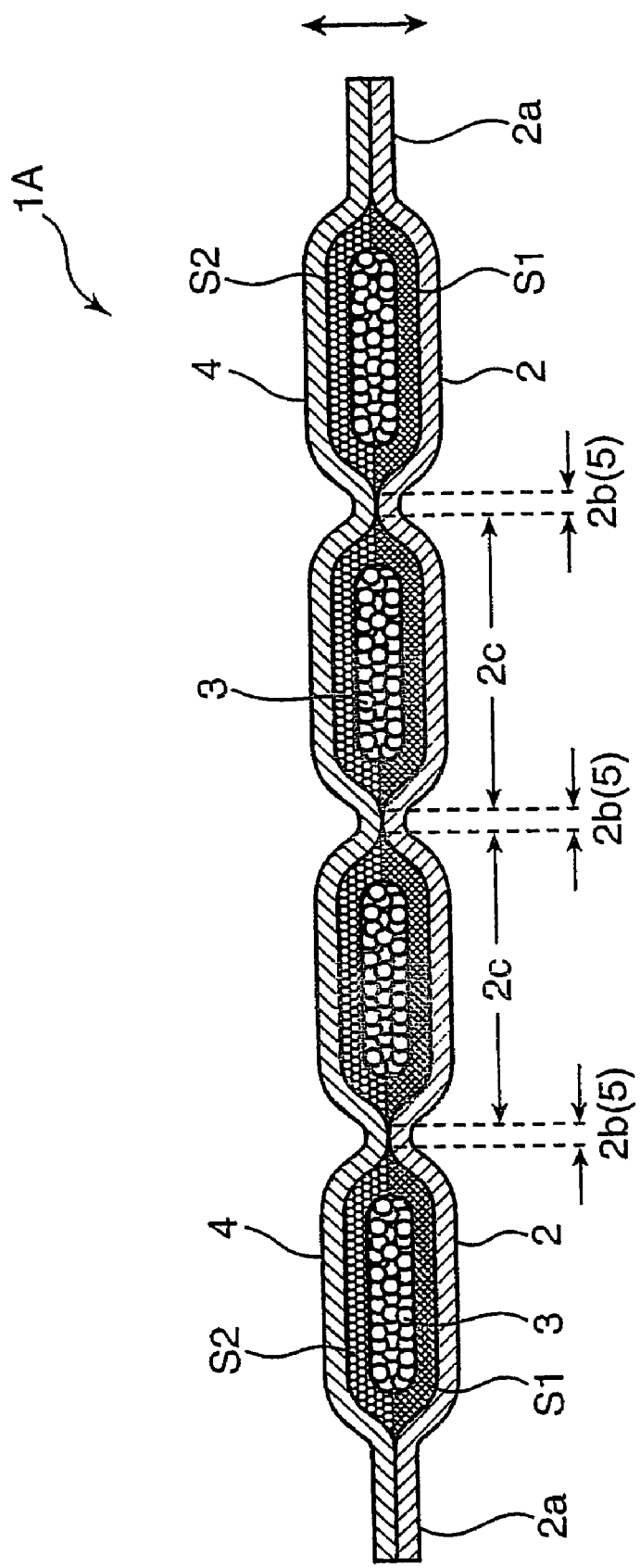
FIG. 2 is a schematic cross-sectional view of the sheet-shaped water-absorbent layer.

Then, the sheet-shaped water-absorbent layer will be described. FIGS. 1 and 2 are a partially cut-out perspective view and a schematic cross-sectional view of the sheet-shaped water-absorbent layer according to a typical embodiment of the present invention, respectively. In FIGS. 2 to 7 and 12, arrows on the right side indicate that an upside is a skin side of the wearer.

The sheet-shaped water-absorbent layer 1A is formed so that the water-absorbent resin powder 3 is held between the first unwoven fabric 2 and the second unwoven fabric 4 having approximately the same area and shape to those of the first unwoven fabric 2. This water-absorbent resin powder 3 is fixedly bonded to the respective unwoven fabrics 2 and 4 by the first adhesive layer S1 applied onto the first unwoven fabric 2 and the second adhesive layer S2 applied onto the second unwoven fabric 4.

Reference symbol 2a denotes a water-absorbent resin powder absence region provided on each end of the sheet-shaped water-absorbent layer 1A in the width direction (hereinafter referred to as the "end region 2a"). Reference symbol 2b denotes a water-absorbent resin powder absence region provided in an intermediate portion of the sheet-shaped water-absorbent layer (hereinafter referred to as the "intermediate region 2b"). Reference symbol 2c denotes a water-absorbent resin powder presence region. In FIG. 1, four water-absorbent resin powder presence regions 2c are provided to be continuous in the longitudinal direction of the first and second nonwoven fabrics 2 and 4 (the outline arrow direction in FIG. 1) and to be separated by the water-absorbent resin powder absence regions 2b in the width direction.

The first and second unwoven fabrics 2 and 4 are joined to each other in the end regions 2a and the intermediate regions 2b in which the water-absorbent resin powder 3 is absent (FIG. 2). That is, the water-absorbent resin powder presence region 2c is partitioned from the adjacent water-absorbent resin powder presence region by the sealing portion 5. FIGS. 1 and 2 show an example in which the adhesive layers S1 and S2 are arranged only in the water-absorbent resin powder presence regions 2c. Alternatively, the adhesive layers S1 and S2 may be arranged in the water-absorbent resin powder absence regions 2b. In addition, the sealing portion 5 may be formed by sealing the region 2c by a heat seal or the like.

The sealing portion 5 should be provided so that at least the two adjacent water-absorbent resin powder presence regions 2c are present independently of each other. After absorbing water, the water-absorbent resin powder 3 swells and is dispersed into the water-absorbent resin powder presence regions 2c. Therefore, even if the water-absorbent resin powder absence regions are formed in the sheet-shaped water-absorbent layer 1A but no sealing portions are present, then a swelling water-absorbent resin layer is formed entirely between the unwoven fabrics forming the sheet-shaped water-absorbent layer, and a space cannot be secured between the sheet-shaped water-absorbent layer and the fiber assembly layer. In addition, the swelling water-absorbent resin inhibits the permeation of a body fluid discharged at the second and subsequent times. For this reason, it is necessary to form the sealing portions 5 so that the water-absorbent resin powder 3 is wrapped in each of the water-absorbent resin powder presence regions 2c. In the water-absorbent resin powder absence regions 2a and 2b sealed by the sealing portions 5, the water-absorbent resin powder may well be present, so long as the powder does not adversely influence sealing.

Figure 3:
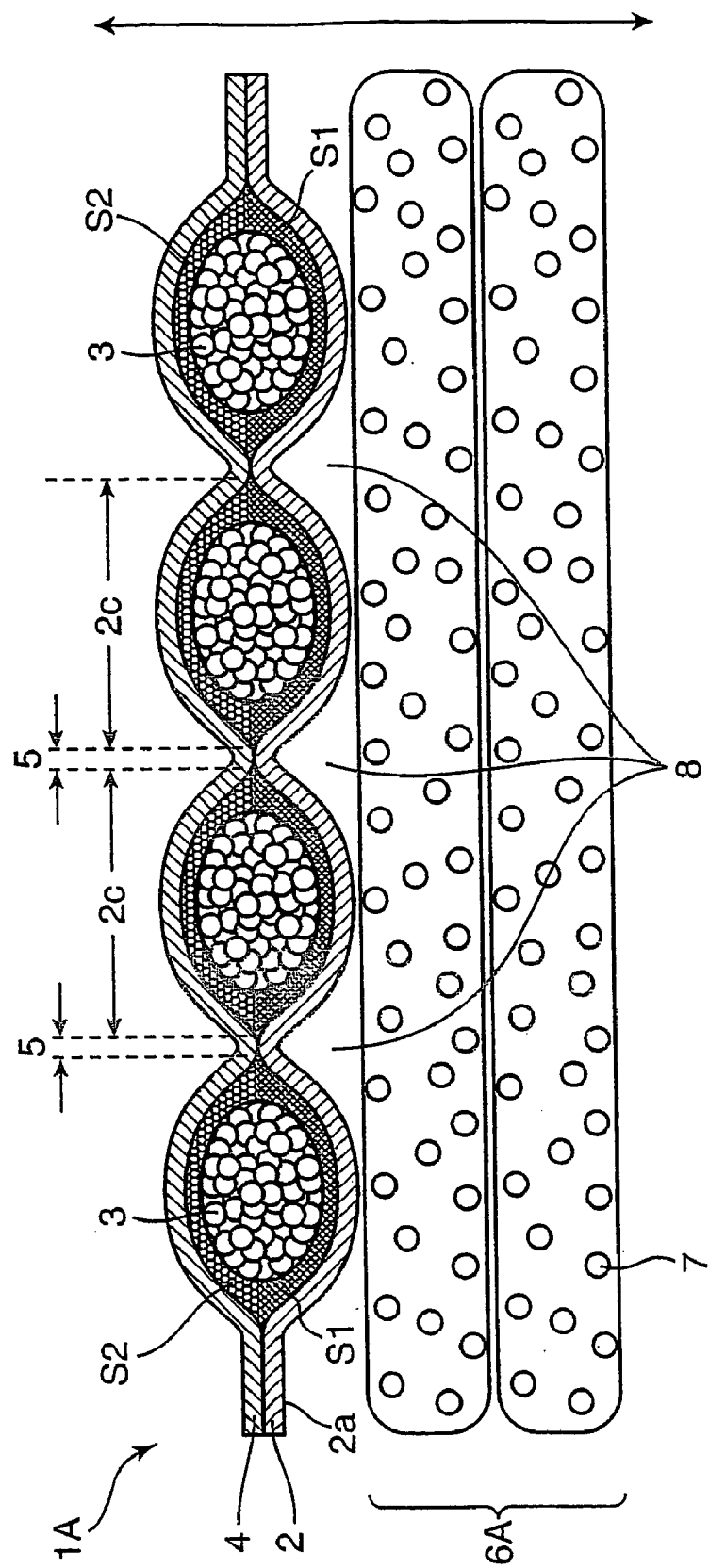
FIG. 3 is a schematic cross-sectional view of an absorbent mat including the swelling sheet-shaped water-absorbent layer.
Figure 4:
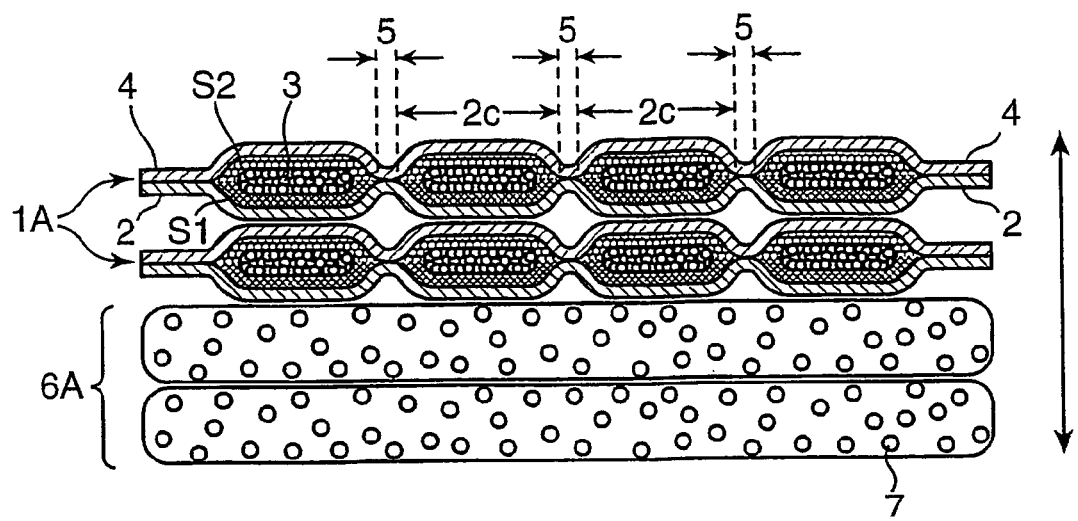
FIG. 4 is a schematic cross-sectional view of an absorbent mat including the sheet-shaped water-absorbent layer having a multilayer structure.

FIG. 3 illustrates a state where an absorbent mat used in the absorbent article of the present invention absorbs a body fluid. The absorbent mat shown in FIG. 3 includes the sheet-shaped water-absorbent layer 1A and the fiber assembly layer 6A provided below the sheet-shaped water-absorbent layer 1A. This fiber assembly layer 6A is formed so that two upper and lower fiber assemblies having approximately the same shape are stacked.

In FIG. 3, the water-absorbent resin powder 3 has absorbed a body fluid excreted from a wearer and has swollen. The water-absorbent resin powder 3 increases the volumes of the water-absorbent resin powder presence regions 2c partitioned by the sealing portions 5 in the range of expansion allowed by the unwoven fabrics 2 and 4, and increases the thickness of the sheet-shaped water-absorbent layer 1A. As a result, the distance between the fiber assembly layer 6A provided below the sheet-shaped water-absorbent layer 1A and the skin of the wearer becomes widened.

In the fiber assembly layer 6A, many cavities are present among fibers, and the water-absorbent resin powder 7 contained in the fiber assembly layer 6A is present to be distributed without concentrating on one portion. During water absorption, therefore, the cavities act as spaces in which the fibers or the water-absorbent resin powder 7 can swell, so that the thickness of the fiber assembly layer 6A is not extremely changed before and after the absorption of the body fluid.

In general, the phenomenon of the backflow (wet back) of a body fluid in the absorbent article is caused by the presence of a fiber assembly layer included in the article. The fiber assembly layer holds the excreted body fluid mainly in the cavities among the fibers. As a result, the body fluid held among the fibers may easily leak out to the surface of the fiber assembly layer when the fiber assembly layer undergoes some pressurization. The water-absorbent resin powder, by contrast, strongly holds the absorbed body fluid in the water-absorbent resin powder (swelling particles). Even if the resin is pressurized, the body fluid absorbed once by the water-absorbent resin powder may hardly leak out again to the surface of the resin.

In the absorbent mat of the absorbent article of the present invention, if the sheet-shaped water-absorbent layer 1A absorbs a body fluid once, the thickness thereof is increased by swelling of the water-absorbent resin powder 3. The distance between the fiber assembly layer 6A serving as the final water holding layer and the skin of the wearer becomes widened. As a result, even if the fiber assembly layer 6A is pressurized and the body fluid leaks out from the fiber assembly layer 6A, it is difficult for this body fluid to overpass the sheet-shaped water-absorbent layer 1A thus thickened and to reach the top sheet 11 (see FIG. 9), thereby effectively suppressing the backflow of the body fluid.

At this time, the sealing portions 5 provided in the water-absorbent resin powder absence regions 2a and 2b gradually rise from their positions before water absorption upward in the thickness direction, following the swelling of the water-absorbent resin powder 3. As a result, spaces 8 are generated between the fiber assembly layer 6A and the sealing portions 5. The body fluid leaking out of the pressurized fiber assembly layer 6A is dispersed in the longitudinal direction of the absorbent article through these spaces 8. The presence of the spaces 8, therefore, also contributes to preventing the backflow of the body fluid.

The spaces 8 generated between the fiber assembly layer 6A and the sheet-shaped water-absorbent layer 1A effectively function when the article is used for a long time or particularly when the article absorbs the body fluid excreted at the second and subsequent times. That is, the amount of water that can be absorbed by the sheet-shaped water-absorbent layer 1A is limited. Therefore, if the body fluid is already absorbed up to the limit amount, a new body fluid cannot be absorbed even when the body fluid is excreted. However, if the spaces 8 are present below the sheet-shaped water-absorbent layer 1A, the body fluid that cannot be absorbed can be dispersed into portions that can still absorb the fluid in the fiber assembly layer 6A through the spaces 8 and absorbed.

Further, since the sheet-like water-absorbent layer 1A prevents the body fluid from passing from the fiber assembly layer 6A to an upside of the sheet-shaped water-absorbent layer 1A, the sheet-shaped water-absorbent layer 1A can contribute to preventing the backflow of the body fluid. That is, when the body fluid is absorbed, the water-absorbent resin powder regions 2c of the sheet-shaped water-absorbent layer 1A are in a state where the swelling water-absorbent resin powder 3 is closely packed, so that it is difficult for the fluid to pass through the regions 2c. Therefore, the body fluid leaking out to the surface of the fiber assembly layer 6A cannot pass through the upside of the sheet-shaped water-absorbent layer 1A and does not flow back.

It is noted, however, that the swelling water-absorbent resin powder presence regions 2c not only prevent the backflow of the body fluid from the fiber assembly layer but also sometimes hinder passing of the newly excreted body fluid to a downside of the sheet-shaped water-absorbent layer 1A. Nevertheless, the sheet-shaped water-absorbent layer 1A according to the present invention includes the sealing portions 5 (intermediate regions 2b) and the water-absorbent resin powder 3 is not present in these sealing portions 5 or even if present, the amount of the powder 3 is quite small. The newly excreted body fluid can, therefore, promptly move to the fiber assembly layer 6A below the sheet-shaped water-absorbent layer 1A through the sealing portions 5. It is possible to ensure absorbing the body fluid excreted at the second and subsequent times.

As described above, in the present invention, the sheet-shaped water-absorbent layer 1A and the fiber assembly layer 6A are formed to have such a structure as described above, whereby it is possible to ensure the sufficient amount of water absorption that enables promptly absorbing even the body fluid excreted at the second and subsequent times. Further, it is possible to suppress the backflow of the body fluid to a low level, prevent the skin of the wearer from being contaminated, and keep the skin clean.

Figure 5:
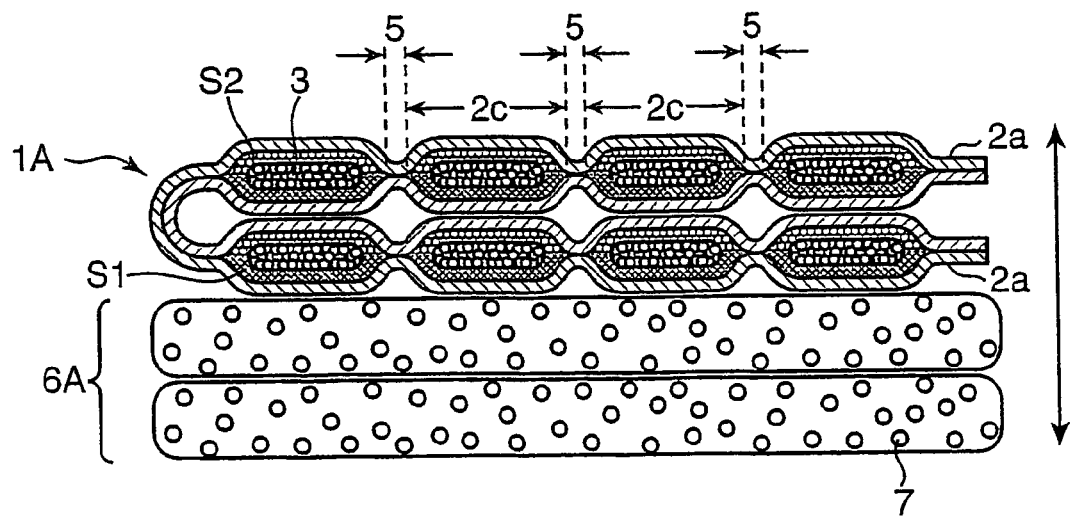
FIG. 5 is a schematic cross-sectional view of an absorbent mat including the sheet-shaped water-absorbent layer having another multilayer structure.
Figure 6:
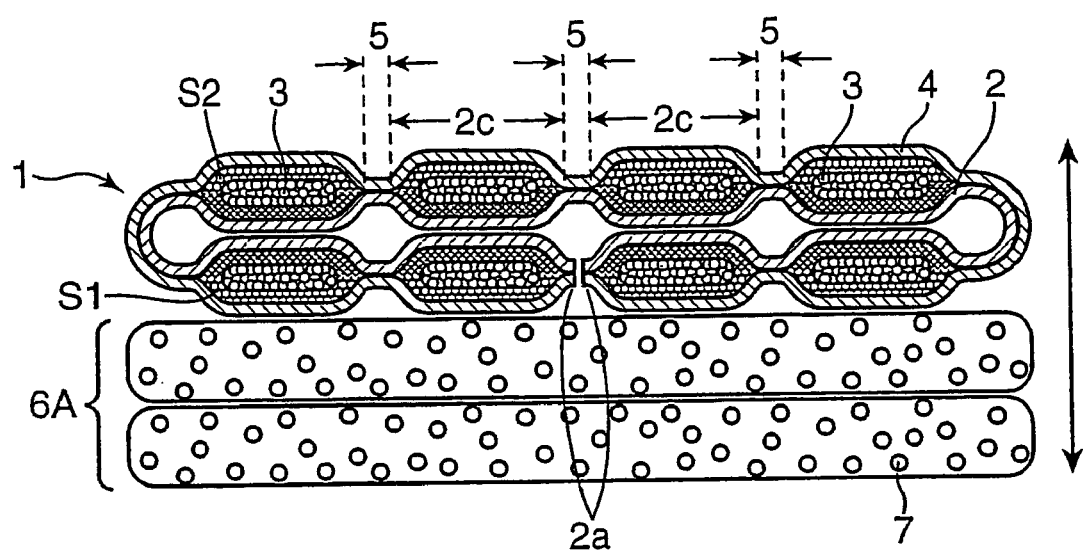
FIG. 6 is a schematic cross-sectional view of an absorbent mat including the sheet-shaped water-absorbent layer having still another multilayer structure.

In the present invention, a multilayer structure of two or more sheet-shaped water-absorbent layers 1A may be provided so as to ensure the sufficient amount of water absorption. The multilayer structure of the two or more sheet-shaped water-absorbent layers 1A may be provided by simply stacking a plurality of sheet-shaped water-absorbent layers 1A (FIG. 4) or by folding a wide sheet-shaped water-absorbent layer 1A (FIGS. 5 and 6). In order to form the folded structure, a single sheet-shaped water-absorbent layer 1A is folded, for example, at the center thereof in the width direction (FIG. 5) or on ends thereof in the width direction downward or upward (FIG. 6). With these embodiments, the multilayer structure can easily be obtained and the necessary amount of water absorption can be secured.

If the sheet-shaped water-absorbent layer 1A having such a multilayer structure is employed, it is preferable that upper and lower water absorbent rein powder presence regions 2c of the sheet-shaped water-absorbent layer 1A are overlapped with each other so as to reduce a backflow amount of the body fluid and to ensure a high absorption speed and a good dispersion performance of the absorbent article. If the water-absorbent resin powder presence region 2c of the upper sheet-shaped water-absorbent layer 1A is overlapped with that of the lower sheet-shaped water-absorbent layer 1A, the thickness of the overall swelling sheet-shaped water-absorbent layers 1A is larger and the distance between the skin of the wearer and the fiber assembly layer becomes wider. The effect of suppressing the fluid backflow phenomenon thereby becomes greater. If the water-absorbent resin powder presence regions 2c are overlapped with the sealing portions 5, the spaces 8 cannot effectively be generated and the body fluid excreted at the second and subsequent times cannot smoothly be absorbed. In order to stably keep the multilayer structure, the respective sheet-shaped water-absorbent layers 1A may preferably be fixedly joined with one another.

Figure 7:
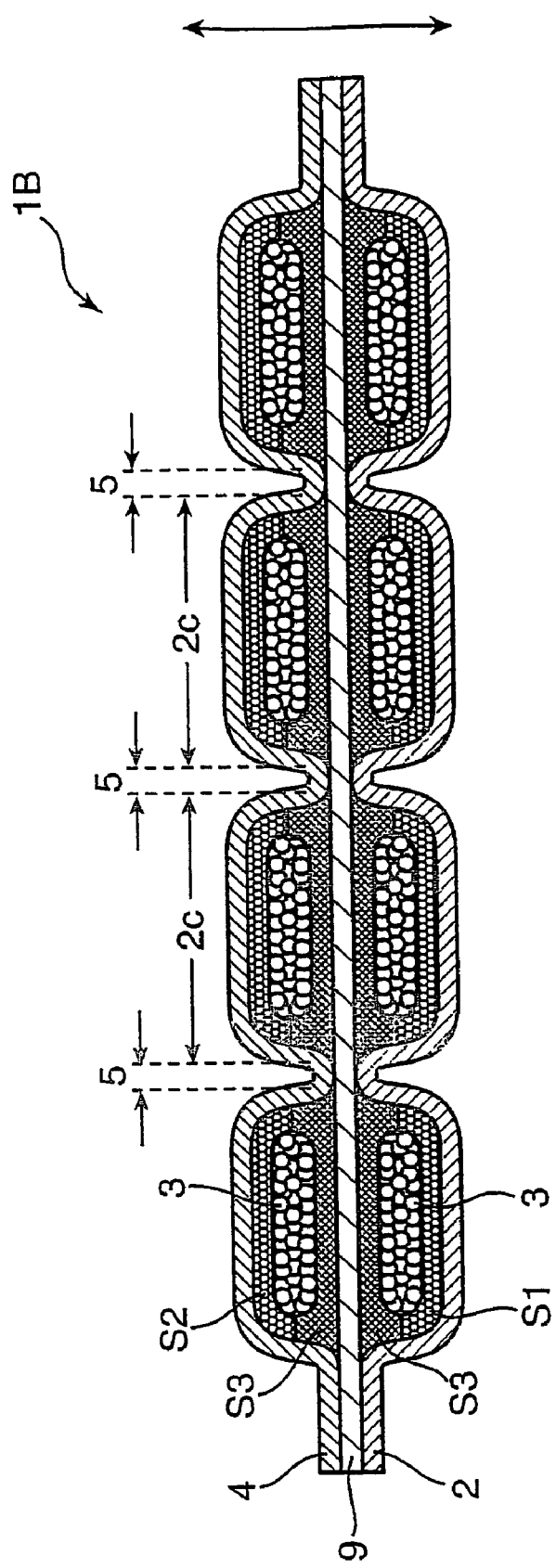
FIG. 7 is a schematic cross-sectional view that illustrates a structure of another sheet-shaped water-absorbent layer.

Alternatively, as shown in FIG. 7, there can also be used a sheet-shaped water-absorbent layer 1B formed so that adhesive layers S1, S2, and S3 are provided between the first unwoven fabric 2 and the intermediate unwoven fabric 9 and between the second unwoven fabric 4 and the intermediate unwoven fabric 9, and so that the water-absorbent resin powder 3 is sealed by the adhesive layers S1, S2, and S3. In this sheet-shaped water-absorbent layer 1B, only one intermediate unwoven fabric 9 is present between the upper and lower water-absorbent resin powders 3 in the thickness direction. Therefore, as compared with the sheet-shaped water-absorbent layers 1A shown in FIGS. 4 to 6, producing steps can be simplified and a cost of the absorbent article itself can be reduced. In addition, as compared with the case of folding the sheet-shaped water-absorbent layer 1A, it is sufficient to produce a narrow sheet and a folding step is unnecessary. Thus, a producing space can be eliminated.

The fiber assembly layer 6A of the absorbent mat explained above has a structure that upper and lower fiber assemblies having approximately the same shape are stacked. Alternatively, the fiber assembly layer 6A may be formed only of one fiber assembly or formed of three or more fiber assemblies. If the fiber assembly layer 6A is too thick, the thickness of the absorbent mat obtained is considerably increased. As a result, the wearer often feels stiff in the hip joint and feels quite uncomfortable after long-time use. The number of stacked layers in the fiber assembly layer 6A may, therefore, appropriately be determined.

Figure 8:
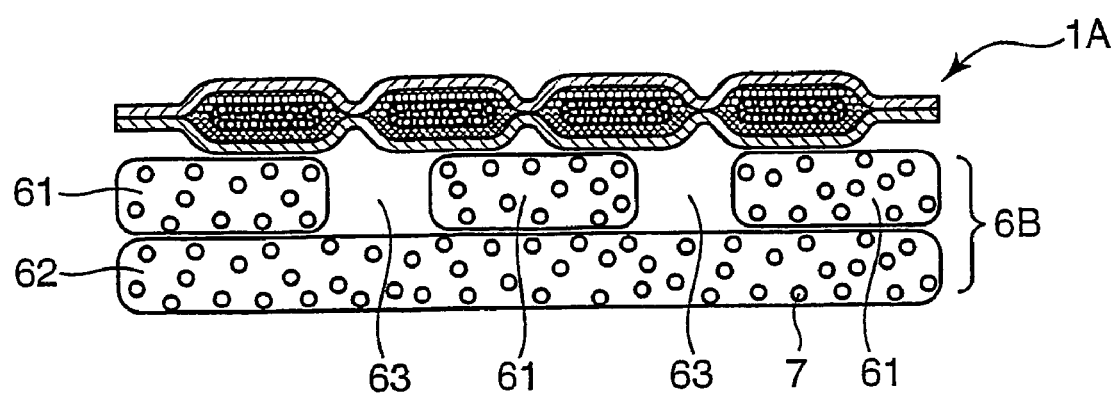
FIG. 8 is a schematic cross-sectional view of an absorbent mat including a fiber assembly having openings.

As the fiber assembly layer, a fiber assembly layer having openings may be used. As a result, it is difficult for the absorbent article to get out of shape and the body fluid absorption speed can be accelerated. FIG. 8 is a cross-sectional view of an absorbent mat formed so that the fiber assembly layer 6B different in formation from the fiber assembly layer 6A is provided below the sheet-shaped water-absorbent layer 1A. This fiber assembly layer 6B is formed so that the upper fiber assembly 61 and the lower fiber assembly 62 equal or smaller in width than the upper fiber assembly 61 are stacked.

The openings 63 formed in the upper fiber assembly 61 shown in FIG. 8 are regions in which neither the pulp fibers nor the water absorbent rein powder are present, so that the openings 63 are low in rigidity. Because of the presence of the openings 63, the upper fiber assembly 61 may easily be deformed. The sheet-shaped water-absorbent layer 1A is originally very thin. Therefore, the absorbent mat thus formed is deformed to follow a body shape or a motion of the wearer but does not get out of shape. This can make it difficult to form a gap between the skin of the wearer and the absorbent mat, thereby advantageously preventing lateral leakage of the body fluid. Moreover, since the lower fiber assembly 62 is always provided below the openings 63, prompt fluid-absorbing operation can be realized, thereby advantageously preventing lateral leakage of the body fluid as well.

Figure 10:
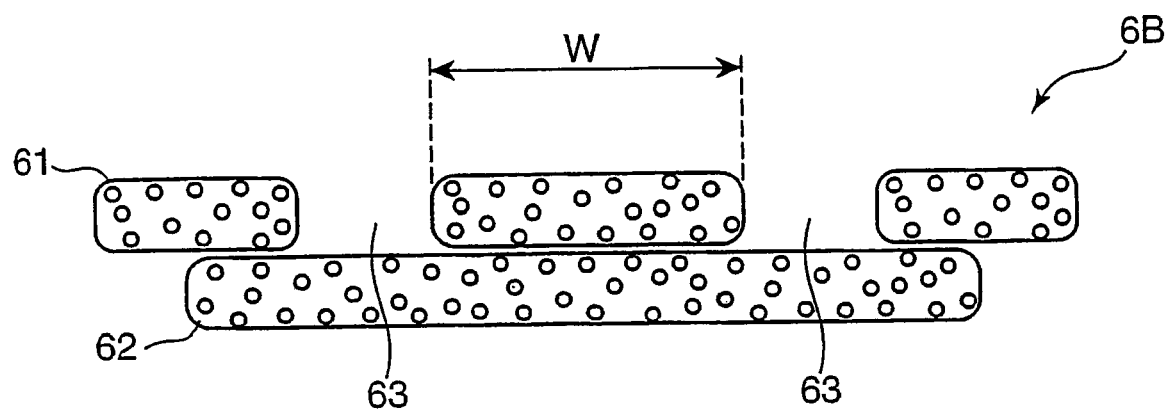
FIG. 10 is a schematic cross-sectional view of the fiber assembly shown in FIG. 9(a) taken along a line Y-Y of FIG. 9(a).

A shape of each opening 63 is not particularly limited to a specific one. FIG. 9(a) shows an example in which two rectangular openings 63 are formed to be continuous in the longitudinal direction of the fiber assembly layer 6B and to be approximately laterally symmetric about the longitudinal center line of the fiber assembly layer 6B at a distance W kept therebetween. FIG. 9(b) shows an example in which six openings 63 are formed intermittently at similar positions to those shown in FIG. 9(a). FIG. 9(c) shows an example in which a ring-shaped opening 63 surrounding the central portion of the upper fiber assembly 61 is formed. FIG. 10 is a sectional view taken along the line Y-Y of FIG. 9(a).

As illustrated in FIGS. 9(a) to 9(c), the openings 63 may preferably be formed in a region other than the central portion of the upper fiber assembly 61. The central portion of the upper fiber assembly 61 refers to a region abutting on an excretion portion of the wearer who wears the absorbent article (a portion corresponding to a urine excretion port and its surroundings). In FIG. 9(a), for example, the central portion of the upper fiber assembly 61 refers to a region having a length indicated by the arrow M and a width indicated by the arrow N. If not the opening 63 but an absorbent component such as fibers is arranged in the portion corresponding to the urine excretion port and its surroundings, the absorbent article becomes bulky and adhesiveness between the wearer and the article is improved. It is, therefore, possible to promptly absorb and hold the excreted urine.

The openings 63 may preferably be formed to extend either continuously or intermittently in the longitudinal direction of the fiber assembly layer 6B since the body fluid can be dispersed throughout the lower fiber assembly 62 through the openings 63. It is also preferable that the openings 63 are formed approximately laterally symmetric about the longitudinal center line of the upper fiber assembly 61 since the absorbent mat can be twisted more easily.

If two or more openings 63 are present in the width direction of the upper fiber assembly 61, the distance W between the two adjacent openings 63 may preferably be 10 mm or greater. If the distance W is too narrow, the absorbent article is not sufficiently fit to the body shape of the wearer even when the upper fiber assembly 61 is bent at the openings 63. The effect of preventing the leakage of the body fluid from the width direction of the absorbent article is reduced. The width W may more preferably be 20 mm or greater, still more preferably 30 mm or greater.

If the above-described formation is employed, the thickness of the fiber assembly layer 6B may preferably be about 2 to 10 mm. The ratio of the thickness of the lower fiber assembly 62 to that of the fiber assembly layer 6B may preferably be about 50%, more preferably about 40%. If the thickness ratio of the lower fiber assembly 62 is greater than 50%, it is difficult to twist the absorbent mat even by providing the openings 63 in the upper fiber assembly 61.

In the fiber assembly layer 6B shown in FIG. 8, the upper fiber assembly 61 and the lower fiber assembly 62 are equal in width. The upper fiber assembly 61 shown in FIG. 9 is approximately gourd-shaped such that the rear portion abutted on the hip of the wearer (left in the figure) is formed wider than the front portion (right side in the figure). The lower fiber assembly 63 is formed into approximately a rectangular shape narrower in width than the upper fiber assembly 61. As can be seen, if the fiber assembly layer 6B having the openings 63 is employed, the lower fiber assembly 62 may preferably b equal to or smaller in width than the upper fiber assembly 61. This is because even if the absorbent mat is twisted, it is difficult for the upper fiber assembly 61 to be offset or to be formed into a mass. In addition, if the upper fiber assembly 61 and the lower fiber assembly 62 are fixed to each other by the hot melt adhesive or the like, the shape of the fiber assembly layer 6B can effectively be retained.

The constituent materials for the sheet-shaped water-absorbent layers 1A and 1B (hereinafter, if the layer is simply referred to as the "sheet-shaped water-absorbent layer 1", the layer 1 represents both the layers 1A and 1B) and the fiber assembly layers 6A and 6B (hereinafter, if the layer is simply referred to as the "fiber assembly layer 6", the layer 6 represents both the layers 6A and 6B) will be described.

As the first nonwoven fabric 2, the second nonwoven fabric 4, and the intermediate nonwoven fabric 9 of the sheet-shaped water-absorbent layer 1, liquid-permeable nonwoven fabrics are used. As fibers forming such nonwoven fabrics, there can be used hydrophilic fibers such as cellulose, rayon, and cotton fibers, and hydrophobic fibers such as polypropylene, polyethylene, polyester, and polyamide fibers, the surface of each of which is subjected to hydrophilic treatment with a surfactant. If the sealing portions 5 are formed of heat seals, heat sealable nonwoven fabrics may be used. As each of the nonwoven fabrics 2 and 4, a plurality of nonwoven fabrics may be stacked.

The first adhesive S1, the second adhesive S2, and the third adhesive S3 are layers for attaching the water-absorbent resin powder 3 onto the nonwoven fabrics 2, 4, and 9, respectively. These adhesive layers S1, S2, and S3 may, therefore, preferably be formed into a net form so that air-permeability in use can be secured without inhibiting the water absorption and swelling of the resin while preventing detachment of the water-absorbent resin powder 3.

As adhesives used for the adhesive layers S1, S2, and S3, the same type or different types of adhesives can be used, and the types are not particularly limited to specific ones. For example, there are used hot melt adhesives such as those of the rubber type, including the natural rubber type, the butyl rubber type, polyisoprene, and the like; styrene-type elastomers, including SIS, SBS, SIBS, SEBS, SEPS, and the like; ethylene-vinyl acetate copolymers (EVA); polyesters; those of the acrylic type; and polyolefin-type elastomers. Each adhesive may preferably have an adhesive force capable of preventing the detachment of the water-absorbent resin after water absorption and has an expansion to be able to follow the swelling of the water-absorbent resin. In these respects, hot melt adhesives of the rubber type or styrene-type elastomers may preferably be used.

To form the adhesive layers S1, S2, and S3 into a net form, a method for discharging a molten adhesive from a plurality of nozzles in a filamentous form (curtain spray method or spiral coating method) is simple and may preferably be used. Specifically, using a curtain spray coater formed so that a plurality of small discharge holes are arranged linearly and so that an air injection port capable of injecting hot air at high speed is provided in the vicinity of each discharge hole, the air is blown off to the molten adhesive discharged from each discharge hole in a filamentous form, whereby the adhesive can be applied as an assembly of nets in which many filamentous adhesives randomly adhere to one another. In addition, using a spiral spray nozzle gun formed so that three or more air injection ports capable of blowing out the air in a direction of the center of nozzle are provided point symmetrically, spiral adhesive layers can be formed on the respective nonwoven fabrics. In the sheet-shaped water-absorbent layer 1A shown in FIG. 1, there is shown an example in which the adhesive layer S1 is applied by the curtain spray method and the adhesive layer S2 is applied by the spiral coating method. Of course, the methods of forming the adhesive layers S1, S2, and S3 are not limited to those shown in FIG. 1, and the adhesive layers S1, S2, and S3 can freely be formed. Each of the adhesive layers S1, S2, and S3 may include a plurality of adhesive application portions or may be applied to the entire surface of the nonwoven fabric.

As the water-absorbent resin powder 3 or 7 used in the sheet-shaped water-absorbent layer 1 or the fiber assembly layer 6, powder composed of a well-known water-absorbent resin can be used. Examples of the well-known water-absorbent resin include those of the polyacrylic acid type, the cellulose type, starch-acrylonitrile type, and the like.

In the sheet-shaped water-absorbent layer 1, the water-absorbent resin powder presence regions 2c are held between the nonwoven fabrics 2 and 4 (or intermediate nonwoven fabric 9) in the up-and-down direction, and the nonwoven fabrics 2 and 4 (or intermediate nonwoven fabric 9) are sealed in the water-absorbent resin powder absence regions 2a and 2b. Therefore, there is a limit to the space in which the water-absorbent resin powder 3 can swell. In order to appropriately carry out the present invention, therefore, the amount of the water-absorbent resin powder 3 may preferably be in the range of 100 g/m$^2$ or greater to 250 g/m$^2$ or smaller, relative to each presence region. If the amount is smaller than 100 g/m$^2$, it is difficult to secure the sufficient water absorbing capacity and maintain the sufficient distance between the fiber assembly layer 6 and the skin of the wearer after swelling. In contrast, if the water-absorbent resin powder 3 is used in an amount of greater than 250 g/m$^2$, it results in an increase of cost. The amount of the water-absorbent resin powder 3 may preferably be in the range of 130 g/m$^2$ or greater to 220 g/m$^2$ or smaller, more preferably in the range of 150 g/m$^2$ or greater to 200 g/m$^2$ or smaller.

After thus forming the adhesive layers S1, S2, and S3 on the respective nonwoven fabrics 2, 4, and 9, and then dispersing the water-absorbent resin powder 3, the nonwoven fabrics 2, 4, and 9 are bonded together and all or part of the water-absorbent resin powder presence regions 2a and 2b are sealed, thereby forming the sealing portions 5.

The sealing portions need to have strength sufficient to prevent breakage by the swelling of the resin. Examples of the means for forming such sealing portions include bonding by a heat seal or hot melt adhesive, ultrasonic bonding, and stitching. Of these, the heat seal is preferred because the nonwoven fabrics 2, 4, and 9 can firmly be bonded together by the heat seals.

If resin powder absence regions other than the end regions 2a and the intermediate regions 2b are provided in parallel to the width direction of the water-absorbent layer 1, these regions may be used as the sealing portions. In this way, it becomes easier to cut the sheet-shaped water absorbing layer 1 in a producing step.

The absorbent mat included in the absorbent article of the present invention is formed by stacking the sheet-shaped water-absorbent layer 1A or 1B on the fiber assembly layer 6A or 6B. In order to prevent the absorbent article from being twisted or deformed during use, the fiber assembly layer 6A or 6B may fixedly be bonded to the sheet-shaped water-absorbent layer 1A or 1B by a means such as an adhesive. It is noted, however, that the adhesive layer may preferably be formed into a net form so as to prevent the generation of the spaces 8 after water absorption and to secure the air-permeability and the like of the absorbent article. As the adhesive used at this time, the same adhesive as that used for the sheet-shaped water-absorbent layer can be used.

Figure 11:
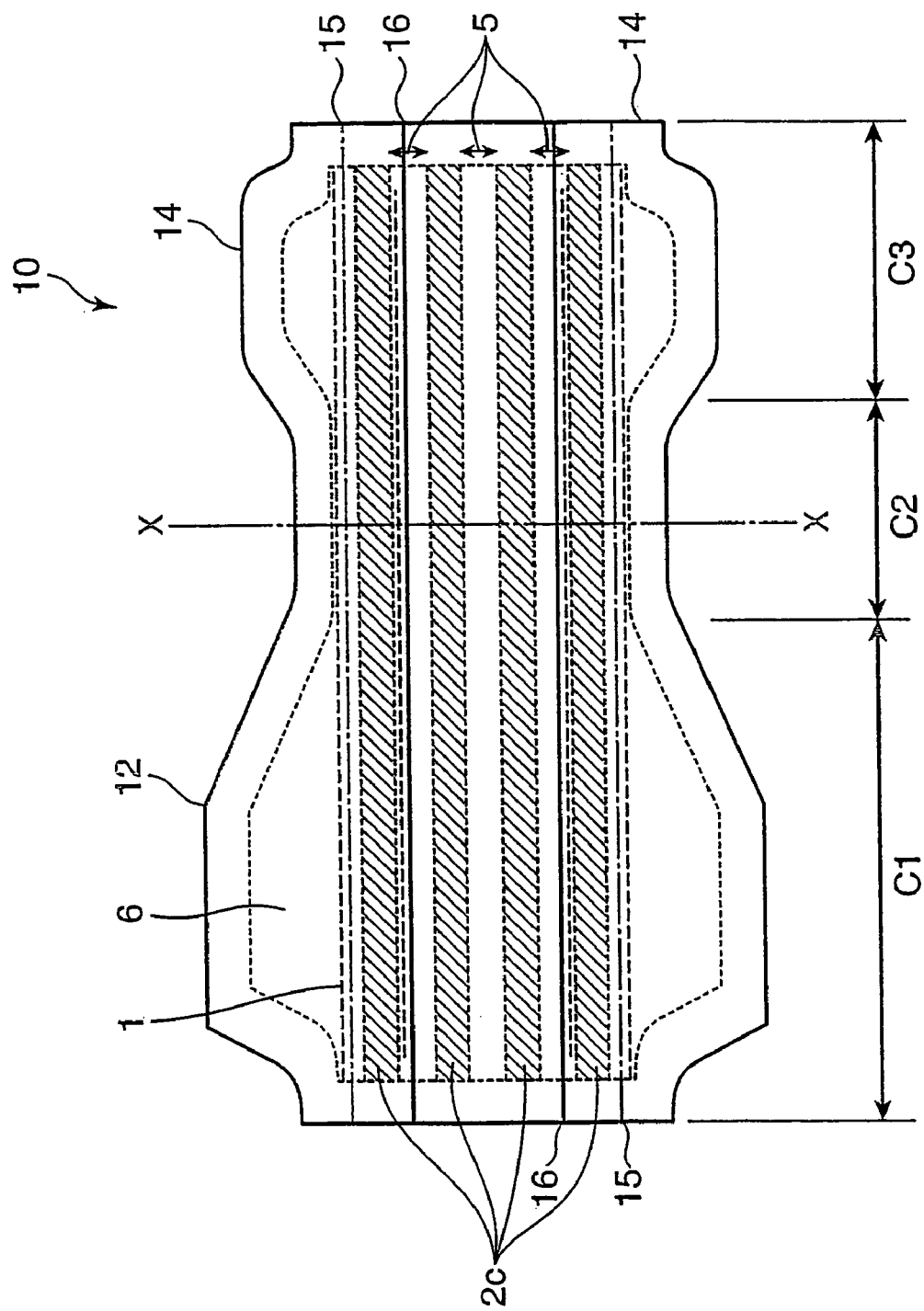
FIG. 11 illustrates a preferred specific example of the absorbent article of the present invention.
Figure 12:
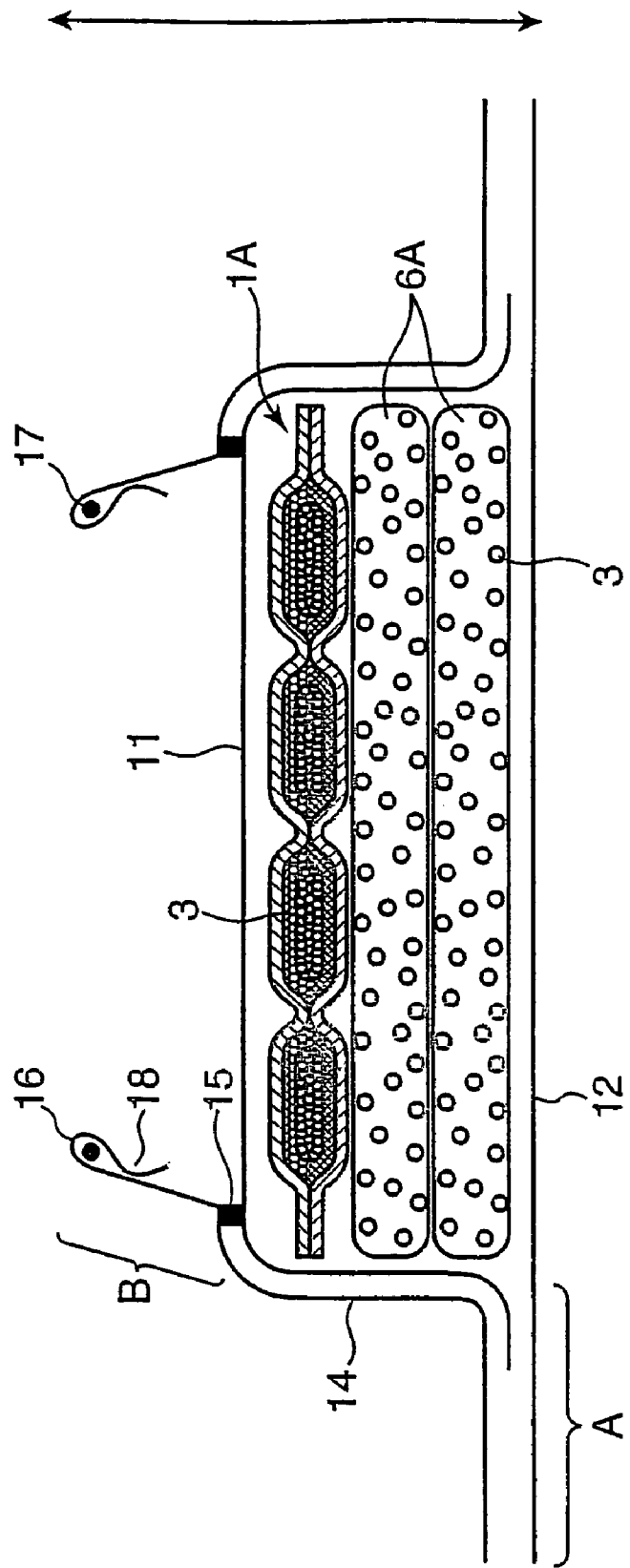
FIG. 12 is a schematic cross-sectional view of the absorbent article taken along a line X-X of FIG. 11.

Using the absorbent mat thus obtained as the absorbent, there are provided absorbent articles such as disposable pants, disposable diapers, and sanitary shorts. FIGS. 11 and 12 illustrate a preferred embodiment of the absorbent article of the present invention. FIG. 12 is a sectional view taken along the ling X-X of FIG. 11. The absorbent article 10 is formed as follows. First, the absorbent mat 13 that includes the sheet-shaped water-absorbent layer 1A (or 1B) and the fiber assembly layer 6A (or 6B) is held between the liquid-permeable top sheet 11 and the liquid-impermeable back sheet 12 so that the sheet-shaped water-absorbent layer 11A is located on the top sheet 11 side. Then, the liquid-impermeable side sheet 14 is provided to cover bottoms and side portions of the absorbent mat 13.

The side sheet 14 is bonded to the top sheet 11 and the back sheet 12 in fixed regions A provided in outer extensions on the bottoms of the absorbent mat 13, respectively. On an upper portion of the absorbent mat 13 (wearer side), the side sheet 14 is bonded to the top sheet 11 on edges (proximal end bonding portions 15) of the absorbent mat 13 in the width direction. Further, the side sheet 14 includes rising regions B rising upward from the respective proximal end portions 15. The side sheet 14 has approximately the same length as that of the absorbent article 10, and is faced down on front and rear ends of the absorbent article 10, and bonded with the upper surface of the top sheet 11 (not shown).

The rising regions B are folded inward in the width direction of the absorbent mat 13 (at inner edges 16), elastic members 17 are provided within the respective inner edges 16 in expanded states, and the side sheets 14 are bonded together in folded bonding portions 18. In such rising regions B, the inner edges 16 rise to follow the skin of the wearer with the proximal end bonding portions 15 used as proximal ends to prevent the lateral leakage of a body fluid to the hip joint when the wearer wears the absorbent article 10.

Since it is necessary to speedily capture a body fluid (excretion) from the wearer and move the body fluid to the absorbent mat 13, a liquid-permeable sheet material may preferably be used for the liquid-permeable top sheet 11. Specifically, examples of the liquid-permeable sheet material include liquid-permeable sheet materials usually used for disposable absorbent articles, such as nonwoven fabrics using hydrophilic fibers such as cellulose, rayon, or cotton fibers, and nonwoven fabrics using hydrophobic fibers such as polypropylene, polyethylene, polyester, or polyamide fibers, the surface of each of which is treated by a surfactant; and plastic films including openings.

To prevent the body fluid absorbed by the absorbent mat from leaking outside the absorbent article 10, water-repellant or liquid-impermeable sheet materials may preferably be used for the liquid-impermeable back sheet 12. More preferably, examples of such materials include water-repellant nonwoven fabrics usually used for disposable diapers (e.g., spunbond nonwoven fabrics, meltblown nonwoven fabrics, and SMS nonwoven fabrics (spunbond-meltblown-spunbond stacked nonwoven fabrics), plastic films (preferably air-permeable plastic films), and composite materials thereof.

As the side sheet 14, water-repellant or liquid-impermeable sheet materials may preferably be used. More preferably, examples of such materials include water-repellant nonwoven fabrics (e.g., spunbond nonwoven fabrics, meltblown nonwoven fabrics, and SMS nonwoven fabrics), air-permeable or air-impermeable plastic films (more preferably air-permeable plastic films), and composite materials thereof.

The proximal end bonding portions 15 for bonding the side sheet 14 to the top sheet 11, the fixed regions A for bonding the side sheet 14 to the back sheet 12, and the folded bonding portions 18 for bonding the side sheets 14 may be bonded by a method such as a heat seal, hot melt adhesive bonding, or ultrasonic bonding.

The elastic members 17 provided in the respective inner edges 16 of the side sheet 14 may be elastic members usually used for disposable diapers and may be, for example, polyurethane or natural rubber. These materials can be used in a filamentous or film form. These elastic members 17 can be provided within the respective inner edges 16 in expanded states by a bonding method such as thermal fusion bonding, hot melt adhesive bonding, or ultrasonic bonding.

In the disposable absorbent article 10 shown in FIG. 11, the lengthwise rear portion C1 abutted on the hip of the wearer when the wearer wears the disposable absorbent article 10 has a shape wide in the width direction enough to cover up the hip. The lengthwise intermediate portion C2 is formed to be narrow in width so as to facilitate close attachment of the portion C2 to the hip joint of the wearer and so as to be tied up to follow the motion of the wearer. Further, the lengthwise front portion C3 is wide in the width direction enough not to make the wearer feel strange. Thus, as a whole, the disposable absorbent article 10 is approximately gourd-shaped. Of course, the whole shape of the disposable absorbent article of the present invention is not limited to the approximately gourd shape, and any shape such as a rectangular shape or an hourglass shape can be applied.

In FIG. 11, there is shown an example in which the absorbent mat 13 is arranged throughout the longitudinal direction of the absorbent article 10. Alternatively, the sheet-shaped water-absorbent layer 1 can be cut off by an appropriate length to partially arrange the cut-off layer at a desired position. For example, the absorbent article may be formed so as to have the sheet-shaped water-absorbent layer 1 provided only in the hip joint.

Then, a preferred example of the method for producing the absorbent mat included in the absorbent article of the present invention will be described. First, a continuous sheet-shaped water-absorbent layer having the sheet-shaped absorbent layer formed continuously in the longitudinal direction is produced on a dedicated sheet-shaped water-absorbent layer producing line, and cut to have a predetermined width, and wound into a roll. On another producing line (which may preferably be an absorbent article producing line) different from the sheet-shaped water-absorbent layer producing line, a continuous body of the fiber assembly layer corresponding to the lower layer of the absorbent mat (continuous fiber assembly layer) is produced. While drawing out the continuous sheet-shaped water-absorbent layer from the roll and allowing the fiber assembly layer to run on the sheet-shaped water-absorbent layer, the hot melt adhesive is applied onto a bonded surface on which the fiber assembly layer is to be bonded to the sheet-shaped water-absorbent layer. While allowing the continuous fiber assembly layer to run, the sheet-shaped water-absorbent layer is mounted on the fiber assembly layer, followed by bonding for integration. The continuous absorbent mat thus obtained is pressurized to stabilize the shape of the mat, and cut to pieces each by a desired size, thereby obtaining individual absorbent mats. Then, the absorbent mats thus obtained are arranged between the liquid-permeable top sheet and the liquid-impermeable back sheet by any of the conventionally well-known methods, thereby forming an absorbent article. If the sheet-shaped water-absorbent layer is smaller in area than the fiber assembly layer, then the hot melt adhesive may be applied to the sheet-shaped water-absorbent layer cut to have a predetermined length in advance, and the resultant sheet-shaped absorbent layer may be transferred onto an appropriate portion on the fiber assembly layer (e.g., the central region of the absorbent article corresponding to the hip join) to provide an absorbent mat, which is then introduced into the absorbent article producing line.

Moreover, if the fiber assembly layers of the respective absorbent articles are produced on the line intermittently, then the sheet-shaped water-absorbent layer cut to have a predetermined length in advance is integrated with the fiber assembly layer to thereby provide an absorbent mat, which is then introduced into the absorbent article producing line to produce an absorbent article similarly to the above method.

To produce continuous or individual fiber assembly layers, the same producing method as that for the well-known absorbent articles can be employed. For example, split pulp fibers and an absorbent resin powder may be attracted and deposited on the circumferential surface of a suction drum provided with recesses (suction regions) corresponding to shapes of desired fiber assemblies. To produce the fiber assembly layer 6B including the upper fiber assembly 61 having the openings 63, non-suction regions corresponding to shapes of the openings 63 may be formed in the recesses on the circumferential surface of the suction drum, and split pulp fibers and an absorbent resin powder may be attracted and deposited on these regions.

If the opening 63 is ring-shaped as shown in FIG. 9(c), then a large opening without the central portion of the upper fiber assembly 61 is provided first in the upper fiber assembly 61, the resultant upper fiber assembly 61 is mounted on the lower fiber assembly 62 formed by a different suction drum, the central portion of the upper fiber assembly 61 is formed by still another suction drum provided downstream, and the central portion thus formed may be mounted at the center of the large opening of the upper fiber assembly 61.

The present invention will be described in more detail with reference to an experimental example. It is noted, however, that the experimental example is not intended to limit the present invention, and that all changes of the experimental example within the scope of the present invention are contained in the technical scope of the present invention.

COMPARATIVE EXAMPLE

Conventional Example

An absorbent article with an absorbent mat was produced, which includes a fiber assembly layer composed of an upper fiber assembly and a lower fiber assembly interposed between a top sheet and a back sheet.

Composite fibers using polyethylene as a sheath and polyester as a core were subjected to hydrophilic treatment with a surfactant, and the hydrophilic composite fibers were cut and carded. Then, the fibers were bonded together by hot air to provide an air-through nonwoven fabric (weight per unit are: 20 g/m$^2$) for use as the top sheet. As the back sheet, a liquid-impermeable polyethylene film having a thickness of 25 μm was used.

A hot melt adhesive (available from Nippon NSC Co., Ltd.; trade name: "MQ-24E"; rubber-type hot melt adhesive) of about 1 to 2 g/m$^2$ was applied in a net form onto tissue paper (weight per unit area: 18 g/m$^2$, size: 410 mm wide×540 mm long). A split pulp fiber core formed by attraction (weight per unit area: about 185 g/m$^2$) was mounted on the hot melt adhesive, and a water-absorbent resin (available from Nippon Shokubai Co., Ltd.; trade name: "CAS601"; polyacrylic acid-type water-absorbent resin) was uniformly dispersed on the split pulp fiber core (dispersion amount: 50 g/m$^2$). Then, the split pulp fiber core and the water-absorbent resin were wrapped up in the tissue paper extending from the edge of the split pulp fiber core in the width direction, thereby providing the lower fiber assembly.

A hot melt adhesive (the same as that used in the lower fiber assembly) of about 1 to 2 g/m$^2$ was applied directly onto the upper surface of this lower fiber assembly in a net form, tissue paper (weight per unit area: 18 g/m$^2$; size: 180 mm wide×540 mm long) was mounted on the hot melt adhesive, and a hot melt adhesive of about 1 to 2 g/m$^2$ was applied onto the tissue paper in a net form. A split pulp fiber core attracted and formed by mixing up water-absorbent resin (the same resin as that used in the lower fiber assembly) of about 78 g/m$^2$ and split pulp fibers (180 to 185 g/m$^2$) were mounted on the hot melt adhesive, thereby providing the upper fiber assembly.

Further, a hot melt adhesive of about 10 to 15 g/m$^2$ was applied onto this upper fiber assembly, and water-absorbent resin was dispersed to have an area of about 83 g/m$^2$, relative to the area of the upper fiber assembly.

The absorbent mat thus obtained was disposed between the top sheet and the back sheet, and the regions having no absorbent mat were bonded by a hot melt adhesive, and an absorbent article of the Comparative Example was produced.

EXAMPLE

Example According to the Present Invention

In this Example, the sheet-shaped water-absorbent layer was used in place of the water-absorbent resin dispersed between the upper fiber assembly and the top sheet in the Comparative Example, and an absorbent article was produced.

The sheet-shaped water-absorbent layer was produced by applying a hot melt adhesive (application amount: 10 g/m$^2$ for both the front and back surfaces) in a net form on the inside surfaces of the first (front surface side) nonwoven fabric and the second (back surface side) nonwoven fabric, and then attaching the water-absorbent resin to the hot melt adhesive.

As the first nonwoven fabric, there was used a "spunlace nonwoven fabric" (weight per unit area: 40 g/m$^2$) obtained by carding and water flow slipping fibers as a mixture of rayon fibers and polyester fibers approximately at a mass ratio of 7:3. As the second nonwoven fabric, there was used an air-through nonwoven fabric (weight per unit area: 20 g/cm²) obtained by subjecting composite fibers using polyethylene as a sheath and polyester as a core to hydrophilic treatment with a surfactant, cutting, and carding the cut fibers, followed by bonding the fibers together by hot air.

The hot melt adhesive was applied so that the width of each water-absorbent resin powder presence region was about 15 to 18 mm on the nonwoven fabric, and was adjusted so that the water-absorbent resin powder absence regions for isolating the respective water-absorbent resin powder presence regions had a width of about 7 to 10 mm. The dispersion amount of the water-absorbent resin in the water-absorbent resin powder presence regions at this time was about 180 g/m².

After bonding the first nonwoven fabric to the second nonwoven fabric, the water-absorbent resin powder absence regions were heat-sealed to thereby form the sealing portions (sealing portion width: about 5 mm), thus producing a sheet-shaped water-absorbent layer.

The total amounts of absorption by the water absorbent article of the Comparative Example and by the water absorbent article of the Example of the present invention were adjusted to be approximately equal.

Using the respective absorbent articles thus obtained, the following backflow measurement was carried out.

Backflow Measurement

Using a 300-cc glass separating funnel, 100 cc of artificial urine (1% sodium chloride aqueous solution) was injected perpendicularly into the neighborhoods of the central portions of the absorbent articles obtained in the Example and in the Comparative Example, respectively, at a breath. A perpendicular distance from the tip end of a dropping portion of the separating funnel to the top sheet of each absorbent article was 3 cm. Simultaneously with the injection, time counting was started. Five minutes later, 10 filter sheets (available from Toyo Roshi Kaisha, Ltd.) having a diameter of 150 mm were put on each injection portion, and a cylindrical weight having a diameter of 150 mm and a total mass of 7 kg was put on the 10 filter sheets. The mass of the filter sheets 6 minutes after the start of injection was measured, the mass (g) of the filter sheets after measurement was subtracted from the mass (g) of the filter sheets before measurement, the numeric value (g) thus obtained was regarded as a backflow amount, and the backflow performance was evaluated using the backflow amount (first measurement).

Ten minutes after the start of the first injection, 100 cc of new artificial urine was injected into the same portion as that at the first measurement at a breath. Five minutes after the start of the second injection (15 minutes after the start of the first injection), 10 new filter sheets were put on the injection portion. Six minutes after the start of the second injection (16 minutes after the start of the first injection), the backflow amount (g) was measured similarly to the first measurement (second measurement).

Figure 13:
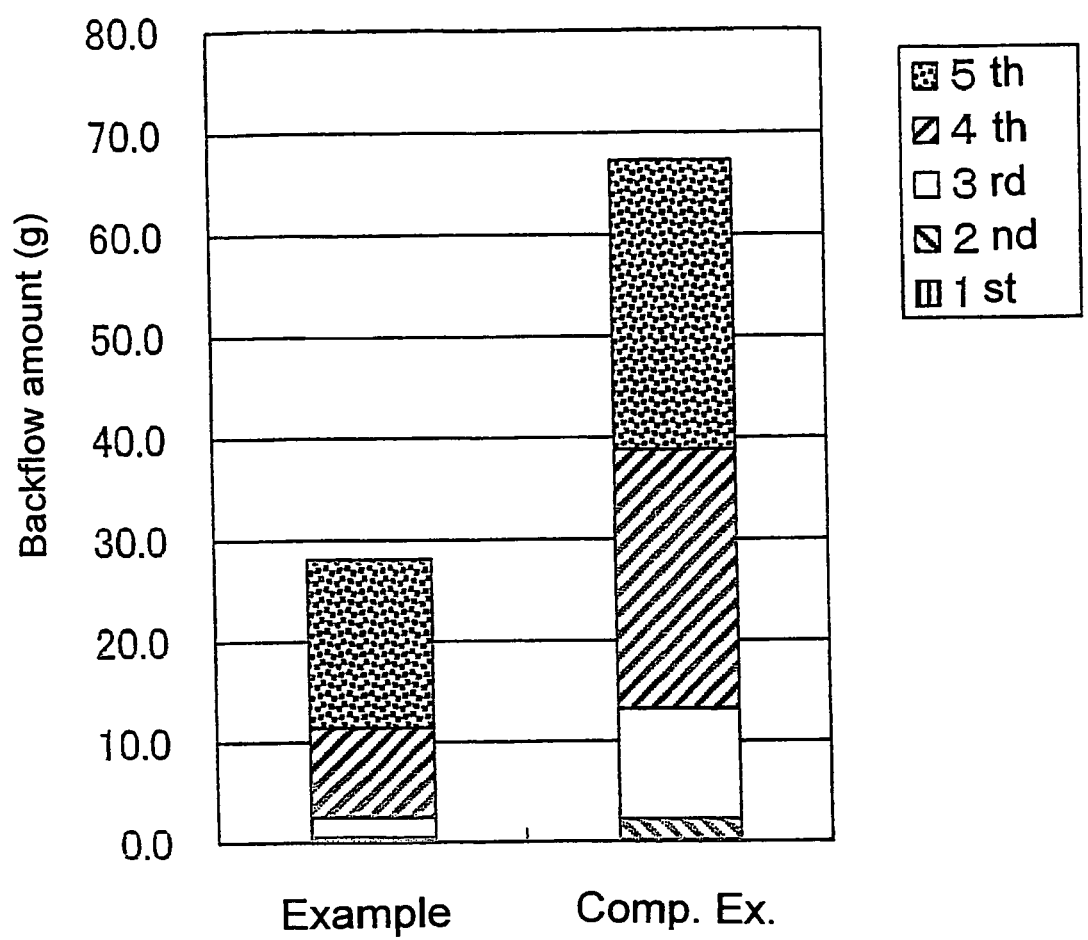
FIG. 13 is a graph that illustrates backflow performance results of the Example and the Comparative Example.

Similarly to the first and second measurements, the backflow amounts were measured at third to fifth measurements. The total injection amount of the artificial urine up to the fifth measurement was 500 cc. The results are shown in Table 1 and FIG. 13.

TABLE 1

|  | 1st | 2nd | 3rd | 4th | 5th | total |
| --- | --- | --- | --- | --- | --- | --- |
| Example | 0.1 | 0.3 | 2.1 | 8.9 | 16.7 | 28.1 (g) |
| Comp. Ex. | 0.1 | 2.1 | 11.0 | 25.6 | 28.5 | 67.3 (g) |

As can be seen from Table 1, as for the absorbent article of the Example, even if the artificial urine was repeatedly injected, the backflow amount was small and an increase of the amount was small. In contrast, as for the absorbent article of the Comparative Example, the absorption amount was increased, as well as the backflow amount was increased, showing that the amount of artificial urine leaking out to the surfaces of the absorbent article was increased.

INDUSTRIAL APPLICABILITY

The absorbent article of the present invention can be used for a long time because of its high absorbing performance. The backflow of the body fluid is suppressed to low level. Therefore, even if the article is used for a long time, the skin of the wearer is not contaminated and kept clean. In addition, the body fluid such as urine can rapidly be absorbed. Even if the absorbent article absorbs a body fluid, it is difficult for the absorbent article to get out of shape. It is thereby possible to make the user who wears the absorbent article feel comfortable, and the absorbent article is useful as disposable diapers or disposable pants.

The invention claimed is:

1. A disposable absorbent article, comprising:
an absorbent mat between a liquid-permeable top sheet and a liquid-impermeable back sheet, the absorbent mat having a top sheet side immediately juxtaposed to the top sheet, the absorbent mat comprising, in the order recited from the top sheet side, a sheet-shaped water-absorbent layer that contains a water-absorbent resin powder but that does not contain pulp fibers; and a fiber assembly layer that contains a water-absorbent resin powder and pulp fibers; wherein
the sheet-shaped water-absorbent layer includes a plurality of water-absorbent resin powder presence regions in each of which the water-absorbent resin powder is wrapped, a plurality of water-absorbent resin powder absence regions each being formed between the two adjacent water-absorbent resin powder presence regions;
the water-absorbent resin powder contained in the sheet-shaped water-absorbent layer is wrapped in a plurality of nonwoven fabrics;
the nonwoven fabrics of the sheet-shaped water-absorbent layer are joined to one another in the water-absorbent resin powder absence regions to form sealing portions; and
the sealing portions are configured so as to be kept completely sealed when the sheet-shaped water-absorbent layer absorbs a bodily fluid.

2. The disposable absorbent article according to claim 1, wherein the nonwoven fabrics of the sheet-shaped water-absorbent layer are molten and attached to one another in the water-absorbent resin powder absence region.

3. The disposable absorbent article according to claim 1, wherein said sheet-shaped water-absorbent layer comprises at least two sheet-shaped water absorbent sheets, the sheet-shaped water absorbent sheets being stacked so that the water-absorbent resin powder presence regions of the sheet-shaped water-absorbent layer substantially overlap on each of said sheet-shaped water absorbent sheets in a thickness direction.

4. The disposable absorbent article according to claim 1, wherein the nonwoven fabrics of the sheet-shaped water-absorbent layer have a rectangular shape having a length, a longitudinal direction and a width direction, and each of the water-absorbent resin powder presence regions extends in the longitudinal direction along the entire length of the nonwoven fabrics, two or more water-absorbent resin powder presence regions are separated by one or more water-absorbent resin powder absence region in the width direction of the nonwoven fabrics.

5. The disposable absorbent article according to claim 4, wherein the sheet-shaped water-absorbent layer comprises
a first nonwoven fabric,
a second nonwoven fabric,
a first adhesive layer fixedly bonded to the first nonwoven fabric,
a second adhesive layer fixedly bonded to the second nonwoven fabric,
the water-absorbent resin powder fixedly bonded to the first nonwoven fabric by the first adhesive layer and fixedly bonded to the second nonwoven fabric by the second adhesive layer, at least one of the first and second adhesive layers having discontinuities in the width direction extending the length of the nonwoven fabrics within each of the one or more water-absorbent resin powder absence regions.

6. The disposable absorbent article according to claim 4, wherein the sheet-shaped water-absorbent layer comprises
a first nonwoven fabric,
a second nonwoven fabric,
a first adhesive layer fixedly bonded to the first nonwoven fabric,
a second adhesive layer fixedly bonded to the second nonwoven fabric,
the water-absorbent resin powder fixedly bonded to the first nonwoven fabric by the first adhesive layer and fixedly bonded to the second nonwoven fabric by the second adhesive layer.

7. The disposable absorbent article according to claim 4, wherein the sheet-shaped water-absorbent layer comprises
a first nonwoven fabric,
a second nonwoven fabric,
a first adhesive layer fixedly bonded to the first nonwoven fabric,
a second adhesive layer fixedly bonded to the second nonwoven fabric,
the water-absorbent resin powder fixedly bonded to the first nonwoven fabric by the first adhesive layer and fixedly bonded to the second nonwoven fabric by the second adhesive layer, the first and second adhesive layers having discontinuities in the width direction extending the length of the nonwoven fabrics within each of the one or more water-absorbent resin powder absence regions.

8. The disposable absorbent article according to claim 1, wherein the fiber assembly layer is formed of an upper fiber assembly and a lower fiber assembly, at least one opening is provided in the upper fiber assembly, and the fiber assembly layer is formed so that the lower fiber assembly is always present below the opening.

9. The disposable absorbent article according to claim 8, wherein the opening is provided in a portion other than a central portion of the upper fiber assembly.

10. The disposable absorbent article according to claim 8, wherein the opening extends in a longitudinal direction of the absorbent article.

11. The disposable absorbent article according to claim 8, wherein the opening is present at a position laterally substantially symmetric about a center line of the upper fiber assembly in the longitudinal direction.

12. A disposable absorbent article, comprising:
a top sheet having a first side;
one or more water-absorbent sheets forming a water-absorbent layer, each of the water-absorbent sheets containing water-absorbent resin powder and not containing pulp fiber, the water absorbent layer having a first water absorbent layer side situated next to the first side of the top sheet and a second water absorbent layer side distal to the first side of the top sheet, wherein the water absorbent sheets comprise:
a first nonwoven fabric
a second nonwoven fabric a plurality of water-absorbent resin powder presence regions in each of which the water-absorbent resin powder is wrapped in between the first nonwoven fabric and the second nonwoven fabric,
a plurality of water-absorbent resin powder absence regions each formed between adjacent water-absorbent resin powder presence regions;
a fiber assembly layer comprised of one or more fiber assemblages, the fiber assembly layer having a first fiber assembly layer side situated next to the second water absorbent layer side and a second fiber assembly layer side distal to the second water absorbent layer side, the fiber assemblages being comprised of water-absorbent resin powder and pulp fibers; and
a liquid-impermeable back sheet situated next to the second fiber assembly layer side, wherein
the first nonwoven fabric and the second nonwoven fabric of the water-absorbent sheets are bonded to one another in the water-absorbent resin powder absence regions to form sealing portions, and the sealing portions are configured so as to be kept completely sealed when the sheet-shaped water-absorbent layer absorbs a bodily fluid.

13. The disposable absorbent article according to claim 12, wherein each of the sheet-shaped water-absorbent sheets comprises a
a first adhesive layer fixedly bonded to the first nonwoven fabric,
a second adhesive layer fixedly bonded to the second nonwoven fabric,
the water-absorbent resin powder fixedly bonded to the first nonwoven fabric by the first adhesive layer and fixedly bonded to the second nonwoven fabric by the second adhesive layer.

14. The disposable absorbent article according to claim 13, wherein two or more water-absorbent sheets form the water-absorbent layer.

15. The disposable absorbent article according to claim 14, wherein the sheet-shaped water absorbent sheets are stacked so that the water-absorbent resin powder presence regions of each of said sheet-shaped water absorbent sheets substantially overlap with the water-absorbent resin powder presence regions of the other sheet-shaped water absorbent sheets in a thickness direction defined by an axis intersecting the top sheet and the back sheet.

16. The disposable absorbent article according to claim 12, wherein a thickness of each of the one or more water-absorbent sheets is greater in the resin powder presence regions than in the resin powder absence regions.

* * * * *